United States Patent [19]

Dostert et al.

[11] Patent Number: 4,476,136
[45] Date of Patent: Oct. 9, 1984

[54] AMINOMETHYL-5 OXAZOLIDINIC DERIVATIVES AND THERAPEUTIC USE THEREOF

[75] Inventors: Philippe L. Dostert, Paris; Alain P. Lacour, La Varenne; Michel Langlois, Buc; Margherita Strolin-Benedetti, Paris, all of France

[73] Assignee: Delalande S.A., Courbevoie, France

[21] Appl. No.: 351,888

[22] Filed: Feb. 24, 1982

[30] Foreign Application Priority Data

Feb. 25, 1981 [FR] France ................................ 81 03797

[51] Int. Cl.³ .................... C07D 263/22; A61K 31/42
[52] U.S. Cl. ...................................... 424/272; 548/229
[58] Field of Search ................. 548/229, 232; 424/272

[56] References Cited

U.S. PATENT DOCUMENTS

| | | | |
|---|---|---|---|
| 3,654,298 | 4/1972 | Douzon et al. | 424/272 |
| 3,687,965 | 8/1972 | Fauran et al. | 424/272 |
| 4,250,318 | 2/1981 | Dostert et al. | 548/229 |
| 4,348,393 | 9/1982 | Bourgery et al. | 548/229 |

FOREIGN PATENT DOCUMENTS 2076813 12/1981 United Kingdom ................ 548/229

Primary Examiner—Robert Gerstl
Assistant Examiner—S. A. Gibson
Attorney, Agent, or Firm—St. Onge, Steward, Johnston & Reens

[57] ABSTRACT

Derivatives corresponding to the general formula:

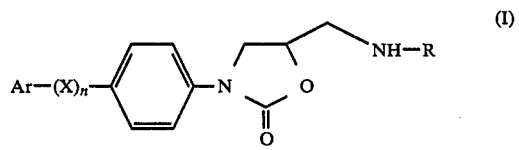

in which Ar represents a phenyl group; a phenyl group substituted by a halogen atom or by a trifluoromethyl group; or the (chloro-3 fluoro-4) phenyl group and n is either equal to zero or equal to 1 in which case X is a chain chosen from the following: —CH$_2$—CH$_2$—, —CH=CH—, —C≡C—, —CH$_2$—O— whose CH$_2$ group is linked to Ar.

These compounds are useful as medicaments more especially for the treatment of troubles of the central nervous system and senescence.

5 Claims, No Drawings

AMINOMETHYL-5 OXAZOLIDINIC DERIVATIVES AND THERAPEUTIC USE THEREOF

The present invention relates to new derivatives of phenyl-3-oxazolidinone-2substituted in position -5by an aminomethyl group, the process for preparing same and the application thereof in therapeutics.

These new derivatives correspond more precisely to the general formula:

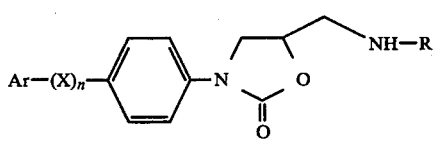

in which:
R represents either a hydrogen atom, or a linear or branched alkyl group comprising from 1 to 4 carbon atoms or a propargyl group,
Ar represents a phenyl group; a phenyl group substituted by a halogen atom or by a trifluoromethyl group; or the (chloro-3fluoro-4) phenyl group; and
n is either equal to zero, or equal to 1 in which case X is a chain chosen from the following: —CH$_2$—CH$_2$—, —CH=CH—, —C≡C—, —CH$_2$—O— the CH$_2$ group of which is linked to Ar;
the pair (Ar, R) not however being able to assume the following values (C$_6$H$_5$, H), (C$_6$H$_5$, CH$_3$), (m—Cl—C$_6$H$_4$, H), (m—Cl—C$_6$H$_4$, CH$_3$), (p—F—C$_6$H$_4$, H), (p—F—C$_6$H$_4$, CH$_3$) when Ar—(X)$_n$ represents the Ar—CH$_2$—O— chain.

The present invention also relates to the acid addition salts of the compounds of formula (I), these acids being able to be mineral such as hydrochloric acid or organic such as mesylic acid.

The process for preparing the compounds of formula (I) consists in:
condensing the amines of formula:

R'—NH$_2$ (II)

in which R' represents a linear or branched alkyl group comprising 1 to 4 carbon atoms or the propargyl group, with the tosylate or mesylate of formula:

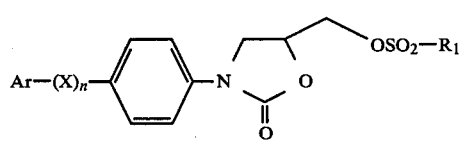

in which AR, X and n have the same meanings as in formula (I) and R$_1$ represents the methyl group or the p-tolyl group, this condensation being preferably carried out in an autoclave at 120° C. and in an alcohol medium such as methanol or ethanol, which leads to the compounds of formula (I) in which R represents a linear or branched alkyl group comprising from 1 to 4 carbon atoms or the propargyl group; and in
condensing potassium phthalamide, at reflux preferably in toluene, in the presence of a so-called "phase transfer" catalyst such as hexadecyltributyl phosphonium bromide for example, on the compounds of formula (III), then in treating the intermediate compounds thus obtained of formula:

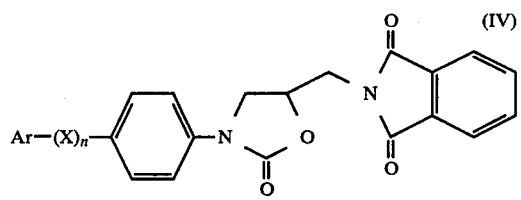

in which Ar, n and X have the same meanings as in formula (I) with hyrazine hydrate at reflux in an alcohol solvent such as ethanol for example, which leads to the compounds of formula (I) in which R=H.

The compounds of formula (III) are obtained by action of mesyl or tosyl chloride, preferably in a methylene chloride medium and in the presence of a basic agent such as triethylamine, on the compounds of formula:

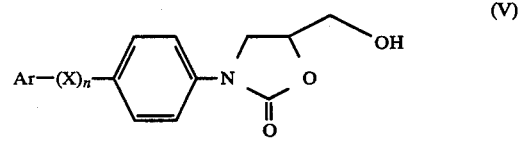

in which Ar, n and X have the same meanings as in formula (I).

The novel compounds of formula (V), namely those in which n=O and those in which n=1 and X represents the —CH=CH— and —CH$_2$—CH$_2$— chains, are obtained from the anilines of formula:

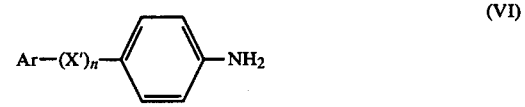

in which Ar has the same meanings as in formula (I) and n is equal to zero or is equal to 1 in which case X' represents the —CH=CH— or —CH$_2$CH$_2$— chain, by a two step synthesis which consists in treating these formula (VI) compounds with glycidol then in cyclizing the intermediate amino-diols obtained with ethyl carbonate.

Certain formula (VI) compounds are new. Thus, those in which n=1, X' represents —CH$_2$—CH$_2$— chain and Ar represents the meta-chlorophenyl, para-chlorophenyl, meta-fluorophenyl, meta-trifluoromethylphenyl and meta-chloro para-fluorophenyl groups are obtained by catalytic reduction, for example in the presence of palladium on charcoal (5 or 10% of palladium) and hydrochloric acid and in an alcohol medium, of the compounds of formula:

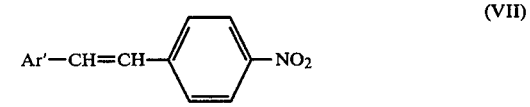

in which Ar' has the meanings just mentioned above.

The compounds of formula (VII) are obtained by condensation of paranitrophenylacetic acid, in the presence of piperidine, with the aldehydes of formula:

     Ar'—CHO     (VIII)

in which Ar' has the meanings as informula (VII).

Furthermore, the novel compounds of formula (V) in which n=1 and X represents the —C≡C— chain are obtained by condensation of the compounds of formula:

    , Ar—C≡C—Cu    (IX)

in which Ar has the same meanings as in formula (I), with the compound of formula:

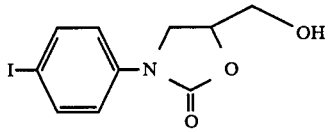    (X)

this condensation taking place preferably in hexamethylenephosphotriamide (H.M.P.T.) at a temperature of 160° C.

The compounds of formula (IX) are prepared according to the method described in Angew. Chem. Int. Edit. 9, 464, (1970), and the compound of formula (X) is prepared by condensation of para-iodoaniline with glycidol, then cyclization of the intermediate compound obtained with ethyl carbonate.

The following preparations are given by way of examples for illustrating the invention.

EXAMPLE 1

N-methylaminomethyl-5 para-(meta-chlorophenetyl) phenyl-3 oxazolidinone-2, hydrochloride (I)

Code number: 7

4.1 g of mesyloxymethyl-5 para-(meta-chlorophenetyl) phenyl-3 oxazolidinone-2 (III) in a methylamine saturated methanol solution is heated to 120° C., for 90 minutes, in an autoclave. Then it is thrown in a mixture of ice, water and NaOH, extracted with chloroform, washed with water, dried on sodium sulfate, filtered, the filtrate is evaporated, the residue dissolved in ethanol, hydrochloric ethanol is added and the precipitate is separated by filtration and washed with ether.

By the same process, but from the corresponding reagents, the compounds of formula (I) were obtained, shown in table I below under code numbers: 9, 12 and 14 to 19.

EXAMPLE 2 aminomethyl-5 para-(meta-chlorophenetyl) phenyl-3 oxazolidinone-2 (I)

Code number: 6

1st step: para-(meta-chlorophenetyl) phenyl-3 (phthalimidyl-2) methyl-5 oxazolidinone-2 (IV)

Code number: 52

A mixture of 9.2 g of mesyloxymethyl-5 para-(meta-chlorophenetyl) phenyl-3 oxazolidinone-2 (III), 5 g of potassium phthalimide and 1.1 g of hexadecyltributylphosphonium bromide in 110 ml of toluene is brought to reflux for 24 hours. Then the solvent is evaporated, the residue taken up in water and chloroform, the obtained solution is decanted, the organic phase is dried on sodium sulfate, filtered, the solvent is evaporated and the residue crystallized in petroleum ether. 98% of the expected product is obtained which has a melting point of 170° C.

By the same process, but from the corresponding reagents, the compounds of formula (IV) are obtained which are required for the synthesis of the compounds of formula (I), and particularly those shown in table II below under code numbers 22 to 32.

2nd step: aminomethyl-5 para-(meta-chlorophenetyl) phenyl-3 oxazolidinone-2 (I)

Code number:6

A suspension of 10.1 g of the compound of formula (IV) obtained in the preceding step and 2.7 g of hydrazine hydrate in 280 ml of alcohol is brought to reflux for 2 hours. Then it is filtered, the filtrate evaporated, the residue is taken up in chloroform, the obtained solution is washed with water, dried with sodium sulfate, filtered, the filtrate is evaporated and the residue is crystallized in petroleum ether.

By the same process, but from the corresponding reagents, the compounds of formula (I) are obtained which are shown in table I under code numbers: 1 to 5, 8, 10, 11, 13, 20 and 21.

EXAMPLE 3 hydroxymethyl-5 para-(para-fluorophenetyl) phenyl-3 oxazolidinone-2 (V)

Code number: 33

A solution of 34 g of para-fluorophenetyl-4 aniline (VI) and 11.7 g of glycidol in 150 ml of ethanol are left in contactat room temperature for 24 hours. Then the solvent is evaporated and the residue chromatographed on a silica column. After elution with the chloroform (97.5%)/methanol (2.5%) mixture, 26 g (Yield ≃57%) of the expected product are obtained which are dissolved in 300 ml of toluene. 8 g of ethyl carbonate and a few drops of a 5% solution of sodium methylate in methanol are added. The mixture is then brought to reflux, while distilling the alcohol formed. Then the toluene solution is concentrated, cooled and the precipitate formed is filtered, washed with ether on the filter and recrystallized in isopropylic alcohol. Thus 13 g of the expected product are obtained.

By the same process, but from the corresponding reagents, the compounds of formula (V) are obtained [which are required for the synthesis of the compounds of formula (I)] shown is table III under code numbers 34 to 39.

EXAMPLE 4 mesyloxymethyl-5 para-(para-fluorophenetyl) phenyl-3 oxazolidinone-2 (III)

Code number: 41

A solution of 12.7 g of the compound of formula (V), code number 33, obtained in the preceding example, 9.1 g of mesyl chloride and 8 g of methylamine in 300 ml of methylene chloride is left at room temperature for 24 hours. Then it is washed with water, dried on sodium sulfate, filtered, the filtrate is evaporated and the residue crystallized in petroleum ether.

By the same process, the compounds of formula (III) are obtained which are required for the synthesis of the compounds of formula (I) and appear in table IV under code numbers 40 and 42 to 51.

EXAMPLE 5 meta-trifluoromethylphenetyl-4 aniline (VI)

Code number: 53

1st step: nitro-4 trifluoromethyl-3' stilbene (VII)

A mixture of 72.4 g of paranitrophenylacetic acid and 69.6 g of meta-trifluoromethylbenzaldehyde is heated to 70° C. Then 34 g of piperidine are slowly added and the solution is brought to 110° C. for 90 minutes. Then it is thrown in 250 ml of ethanol, the precipitate obtained is filtered and rinced with alcohol. 22% of the expected product is obtained which is yellow and whose melting point is 120° C.

2nd step: meta-trifluoromethylphenetyl-4 aniline (VI)

A suspension of 26 g of the compound of formula (VII) obtained in the preceding step and 2.6 g of palladium on charcoal (5% of palladium) in 400 ml of ethanol and 100 ml of T.H.F. is brought to 30° C., at a pressure of 3 kg of hydrogen, in an autoclave. Then it is filtered and the filtrate evaporated. 94% of an oil is obtained which is used for preparing the corresponding compound of formula (V), according to the method described in example 3.

NMR spectrum: (CDCl$_3$)

$\delta$ppm=7.35, m, 4 aromatic protons; 6.90, d, (J=7 Hz) and 6.45, d, (J=7 Hz), 4 aromatic protons; 3.40, s, 2 NH$_2$ protons; 2.80, s, 4—CH$_2$—CH$_2$— protons.

By the same process, but from the corresponding reagents, the compounds of formula (VI) are obtained which are required for the synthesis of the compounds of formula (I) and more especially the following:

4-(para-fluorophenetyl) aniline [code number 54, melting point 93° C.]

4(meta-fluorophenetyl) aniline [code number 55, melting point 54° C.]

4-(para-chlorophenetyl) aniline [code number 56, melting point 90° C.]

4-(meta-chloro para-fluorophenetyl) aniline [code number 57, melting point 73° C.].

EXAMPLE 6 para [(meta-chlorophenyl)-1 ethynyl-2 ] phenyl-3 hydroxymethyl-5 oxazolidinone-2 (V)

Code number: 58

A suspension of 10.8 g of the copper salt of meta-chlorophenyl-1 ethynyl (IX) and 14.7 g of para-iodophenyl-3 hydroxymethyl-5 oxazolidinone-2 (X) in 230 ml of H.M.P.T. is brought to 160° C. until complete dissolution is obtained. Then it is allowed to cool to room temperature, thrown in water, the obtained mixture is extracted with ethyl acetate, the extract is washed with water, dried on sodium sulfate, filtered, the filtrate is evaporated and the residue crystallized in a mixture of 150 ml of isopropylic ether and 20 ml of ether. 11.5 g of the expected product are obtained.

Yield: 76%

Melting point: 96° C.

TABLE I

Ar—(X)$_n$—[phenyl]—N(C=O)O—CH(CH$_2$NH—R)— (I)

| Number | Code Ar—(X)$_n$— | R | Form | Empirical formula | Molecular weight | Melting point (°C.) | Yield (%) | ELEMENTARY ANALYSIS % | C | H | N |
|---|---|---|---|---|---|---|---|---|---|---|---|
| 1 | Cl—[phenyl]— | H | Base | C$_{16}$H$_{15}$ClN$_2$O$_2$ | 302.75 | 153 | 82 | Cal. Obt. | 63.47 63.05 | 4.99 4.69 | 9.25 9.05 |
| 2 | [phenyl]—CH$_2$—CH$_2$— | " | Hydrated base | C$_{18}$H$_{20}$N$_2$O$_2$ + 0.9% H$_2$O | 299.05 | 115 | 76 | Cal. Obt. | 72.29 72.40 | 6.84 6.90 | 9.36 9.32 |
| 3 | F—[phenyl]—CH$_2$—CH$_2$— | " | Base | C$_{18}$H$_{19}$FN$_2$O$_2$ | 314.35 | 98 | 67 | Cal. Obt. | 68.77 68.58 | 6.09 6.38 | 8.91 8.81 |
| 4 | F[phenyl]—CH$_2$—CH$_2$— | " | Base | C$_{18}$H$_{19}$FN$_2$O$_2$ | 314.35 | 80 | 71 | Cal. Obt. | 68.77 68.61 | 6.09 6.37 | 8.91 9.05 |
| 5 | Cl—[phenyl]—CH$_2$—CH$_2$— | " | Base | C$_{18}$H$_{19}$ClN$_2$O$_2$ | 330.80 | 80 | 50 | Cal. Obt. | 65.35 65.05 | 5.79 5.61 | 8.47 8.47 |
| 6 | Cl[phenyl]—CH$_2$—CH$_2$— | " | " | C$_{18}$H$_{19}$ClN$_2$O$_2$ | 330.80 | 79 | 56 | Cal. Obt. | 65.35 64.57 | 5.79 5.93 | 8.47 8.28 |
| 7 | " | —CH$_3$ | HCl | C$_{19}$H$_{22}$Cl$_2$N$_2$O$_2$ | 381.29 | 226 | 84 | Cal. Obt. | 59.85 59.52 | 5.82 5.73 | 7.35 7.44 |
| 8 | Cl,F[phenyl]—CH$_2$—CH$_2$— | —H | HCl | C$_{18}$H$_{19}$Cl$_2$FN$_2$O$_2$ | 385.26 | 170 | 62 | Cal. Obt. | 56.11 56.41 | 4.97 5.24 | 7.27 7.11 |

TABLE I-continued

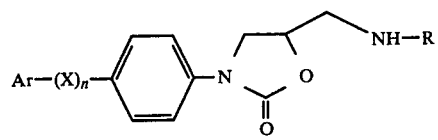
(I)

| Number | Code Ar—(X)$_n$— | R | Form | Empirical formula | Molecular weight | Melting point (°C.) | Yield (%) | ELEMENTARY ANALYSIS % | C | H | N |
|---|---|---|---|---|---|---|---|---|---|---|---|
| 9 | Cl, F-phenyl-CH$_2$—CH$_2$— | —CH$_3$ | HCl | C$_{19}$H$_{21}$Cl$_2$FN$_2$O$_2$ | 399.29 | 188 | 50 | Cal.<br>Obt. | 57.15<br>57.20 | 5.30<br>5.26 | 7.02<br>6.89 |
| 10 | CF$_3$-phenyl-CH$_2$—CH$_2$— | —H | " | C$_{19}$H$_{20}$ClF$_3$N$_2$O$_2$ | 400.83 | >260 | 68 | Cal.<br>Obt. | 56.93<br>56.69 | 5.03<br>4.95 | 6.99<br>6.93 |
| 11 | Cl-phenyl-CH=CH— | " | " | C$_{18}$H$_{19}$Cl$_2$N$_2$O$_2$ | 365.25 | >260 | 48 | Cal.<br>Obt. | 59.19<br>58.90 | 4.97<br>4.96 | 7.64<br>7.64 |
| 12 | " | —CH$_3$ | " | C$_{19}$H$_{20}$Cl$_2$N$_2$O$_2$ | 379.28 | >260 | 62 | Cal.<br>Obt. | 60.17<br>59.74 | 5.32<br>5.26 | 7.39<br>7.21 |
| 13 | Cl-phenyl-C≡C— | —H | Base | C$_{18}$H$_{15}$ClN$_2$O$_2$ | 328.77 | 82 | 18 | Cal.<br>Obt. | 65.75<br>65.08 | 4.60<br>4.92 | 8.52<br>8.48 |
| 14 | " | —CH$_3$ | " | C$_{19}$H$_{17}$ClN$_2$O$_2$ | 340.79 | 106 | 14 | Cal.<br>Obt. | 66.96<br>66.86 | 5.03<br>5.35 | 8.22<br>8.13 |
| 15 | Cl-phenyl-CH$_2$—O— | —Et | HCl | C$_{19}$H$_{22}$Cl$_2$N$_2$O$_3$ | 397.29 | 232 | 74 | Cal.<br>Obt. | 57.44<br>57.20 | 5.58<br>5.49 | 7.05<br>6.93 |
| 16 | " | —C$_3$H$_{7n}$ | Hydrated HCl | C$_{20}$H$_{24}$Cl$_2$N$_2$O$_3$ + 0.8% H$_2$O | 414.71 | 217 | 68 | Cal.<br>Obt. | 57.92<br>57.86 | 5.92<br>5.66 | 6.75<br>6.52 |
| 17 | " | —C$_3$H$_7$iso | HCl | C$_{20}$H$_{24}$Cl$_2$N$_2$O$_3$ | 411.32 | 212 | 51 | Cal.<br>Obt. | 58.40<br>58.34 | 5.88<br>5.71 | 6.81<br>6.62 |
| 18 | " | —C$_4$H$_{9n}$ | " | C$_{21}$H$_{26}$Cl$_2$N$_2$O$_3$ | 425.35 | 228 | 66 | Cal.<br>Obt. | 59.29<br>58.98 | 6.16<br>5.97 | 6.59<br>6.44 |
| 19 | " | —CH$_2$—C≡CH | " | C$_{20}$H$_{20}$Cl$_2$N$_2$O$_3$ | 407.29 | 212 | 55 | Cal.<br>Obt. | 58.98<br>58.68 | 4.95<br>5.10 | 6.88<br>6.61 |
| 20 | CF$_3$-phenyl-CH$_2$—O— | —H | " | C$_{18}$H$_{18}$ClF$_3$N$_2$O$_3$ | 402.79 | 210 | 76 | Cal.<br>Obt. | 53.67<br>53.78 | 4.25<br>4.01 | 6.96<br>6.97 |
| 21 | Cl, F-phenyl-CH$_2$—O— | —H | Mesylate | C$_{18}$H$_{20}$ClFN$_2$O$_6$S | 446.88 | 198 | 58 | Cal.<br>Obt. | 48.38<br>48.09 | 4.51<br>4.47 | 6.27<br>6.34 |

TABLE II

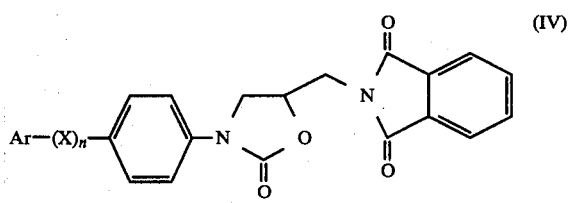

(IV)

| Code Number | Ar—(X)$_n$— | Empirical formula | Molecular weight | Melting point (°C.) |
|---|---|---|---|---|
| 22 | ⌬—CH$_2$—CH$_2$— | C$_{26}$H$_{22}$N$_2$O$_4$ | 426.45 | 210 |
| 23 | F—⌬—CH$_2$—CH$_2$— | C$_{26}$H$_{21}$FN$_2$O$_4$ | 444.44 | 217 |
| 24 | F-⌬—CH$_2$—CH$_2$— | C$_{26}$H$_{21}$FN$_2$O$_4$ | 444.44 | 184 |
| 25 | Cl—⌬—CH$_2$—CH$_2$— | C$_{26}$H$_{21}$ClN$_2$O$_4$ | 460.90 | 244 |
| 26 | Cl,F-⌬—CH$_2$—CH$_2$— | C$_{26}$H$_{20}$ClFN$_2$O$_4$ | 478.89 | 196 |
| 27 | CF$_3$-⌬—CH$_2$—CH$_2$— | C$_{27}$H$_{21}$F$_3$N$_2$O$_4$ | 494.45 | 165 |
| 28 | Cl—⌬— | C$_{24}$H$_{17}$ClN$_2$O$_4$ | 432.85 | 260 |
| 29 | Cl-⌬—CH=CH— | C$_{26}$H$_{19}$ClN$_2$O$_4$ | 458.88 | 220 |
| 30 | Cl-⌬—C≡C— | C$_{26}$H$_{17}$ClN$_2$O$_4$ | 456.87 | 188 |
| 31 | CF$_3$-⌬—CH$_2$—O— | C$_{26}$H$_{19}$F$_3$N$_2$O$_5$ | 528.49 | 164 |
| 32 | Cl,F-⌬—CH$_2$—O— | C$_{25}$H$_{18}$ClFN$_2$O$_5$ | 480.87 | 170 |

TABLE III

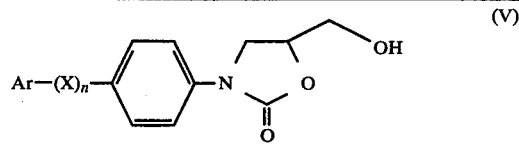

(V)

| Code Number | Ar—(X)$_n$— | Empirical formula | Molecular weight | Melting point (°C.) |
|---|---|---|---|---|
| 33 | F—⌬—CH$_2$—CH$_2$— | C$_{18}$H$_{18}$FNO$_3$ | 315.33 | 131 |
| 34 | F-⌬—CH$_2$—CH$_2$— | C$_{18}$H$_{18}$FNO$_3$ | 315.33 | 116 |
| 35 | Cl—⌬—CH$_2$CH$_2$— | C$_{18}$H$_{18}$ClNO$_3$ | 331.79 | 131 |
| 36 | Cl,F-⌬—CH$_2$—CH$_2$— | C$_{17}$H$_{15}$ClFNO$_3$ | 335.77 | 120 |
| 37 | CF$_3$-⌬—CH$_2$—CH$_2$— | C$_{19}$H$_{18}$F$_3$NO$_2$ | 349.34 | 120 |
| 38 | Cl-⌬—CH=CH— | C$_{18}$H$_{16}$ClNO$_3$ | 329.77 | 96 |
| 39 | Cl—⌬— | C$_{16}$H$_{14}$ClNO$_3$ | 303.74 | 170 |

TABLE IV

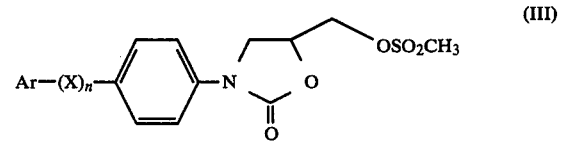

(III)

| Code Number | Ar—(X)$_n$— | Empirical formula | Molecular weight | Melting point (°C.) |
|---|---|---|---|---|
| 40 | ⌬—CH$_2$—CH$_2$— | C$_{19}$H$_{21}$NO$_5$S | 375.43 | 174 |
| 41 | F—⌬—CH$_2$—CH$_2$— | C$_{19}$H$_{20}$FNO$_5$S | 393.42 | 158 |
| 42 | F-⌬—CH$_2$—CH$_2$— | C$_{19}$H$_{20}$FNO$_5$S | 393.42 | 168 |
| 43 | Cl—⌬—CH$_2$—CH$_2$— | C$_{19}$H$_{20}$ClNO$_5$S | 409.88 | 150 |
| 44 | Cl,F-⌬—CH$_2$—CH$_2$— | C$_{19}$H$_{19}$ClFNO$_5$S | 427.87 | 136 |

TABLE IV-continued $$Ar-(X)_n-\bigcirc-N\underset{O}{\overset{O}{\diagup}}-OSO_2CH_3 \quad (III)$$

| Code Number | Ar—(X)$_n$— | Empirical formula | Molecular weight | Melting point (°C.) |
|---|---|---|---|---|
| 45 | CF$_3$-⌬-CH$_2$-CH$_2$- | C$_{20}$H$_{20}$F$_3$NO$_5$S | 443.43 | 99 |
| 46 | Cl-⌬-CH$_2$-CH$_2$- | C$_{19}$H$_{20}$ClNO$_5$S | 409.88 | 149 |
| 47 | Cl-⌬- | C$_{17}$H$_{16}$ClNO$_5$S | 381.83 | 197 |
| 48 | Cl-⌬-CH=CH— | C$_{19}$H$_{18}$ClNO$_5$S | 407.86 | 200 |
| 49 | Cl-⌬-C≡C— | C$_{19}$H$_{16}$ClNO$_5$S | 405.85 | 164 |
| 50 | CF$_3$-⌬-CH$_2$-O— | C$_{19}$H$_{18}$F$_3$NO$_6$S | 445.41 | 128 |
| 51 | Cl,F-⌬-CH$_2$-O— | C$_{18}$H$_{17}$ClFNO$_6$S | 429.85 | 122 |

The compounds of formula (I) and their pharmaceutically acceptable acid addition salts were tested on laboratory animals and revealed to be able to inhibit the monoamine oxydase, particularly the type B monoamine oxydase.

This activity was demonstrated ex vivo on rats to which a single dose of the compounds of formula (I) or their salts in suspension at 5% in methylcellulose was administered orally. Then the rats were sacrificed by decapitating them at different times (30 minutes, 1 hour, 2 hours, 4 hours, 8 hours, 24 hours after administration). The brains were removed, weighed and homogenized and determination of the IMAO activity is effected by using serotonine (a specific substrate of MAO of type (A) and phenylethylamine (a specific substrate of MAO of type B) according to the method described by J.P. KAN and M. STROLIN-BENEDETTI in Life Sciences 26, 2165, (1980).

To illustrate the invention, there is given in table V below the results obtained in this test for some compounds of the invention [the maximum effect is that observed between 30 minutes and 8 hours].

Acute toxicity in mice, under oral administration, was measured according to the method of MILLER and TAINTER described in Proc. Soc. Exp. Biol. Med. 57, 261, (1944).

TABLE V

| Compound tested | Acute toxicity in mice LD 50(mg/Kg/p.o.) | Dose administered (mg/Kg/p.o.) | IMAO effect | | | | | |
|---|---|---|---|---|---|---|---|---|
| | | | IMAO-A effect | | | IMAO-B effect | | |
| | | | Max. | 8h | 24h | Max. | 8h | 24h |
| 4 | >2.000 | 5 | 16 | 1 | 0 | 56 | 46 | 53 |
| 6 | " | 5 | 30 | 11 | 0 | 91 | 90 | 79 |
| | | 2.5 | 11 | 3 | 4 | 64 | 64 | 57 |
| 8 | " | 5 | 24 | 18 | 2 | 82 | 81 | 51 |
| 10 | " | 5 | 19 | 18 | 3 | 87 | 87 | 81 |
| 12 | " | 5 | 19 | 19 | 13 | 87 | 74 | 85 |
| 16 | " | 5 | 17 | 12 | 6 | 73 | 66 | 52 |
| 19 | " | 5 | 17 | 14 | 0 | 87 | 87 | 74 |

The difference between toxic doses and active doses shows that the compounds of the invention can be used in therapeutics. They will be used for (a) troubles of the central nervous system treated by inhibitors of the B type monoamine oxydase, particularly in association with L-DOPA in the treatment of PARKINSON's disease [see, for example, Isr. J. Med. Sci. 15, 617 (1979); Adv. in Biochem. Psychopharm. 19, 377; Brit. J. Chem. Pharmacol. 9, 98, (1980]and (b) for senescence troubles.

The invention extends to pharmaceutical compositions including, as active ingredient, one at least of the compounds of the invention in association with a pharmaceutically acceptable vehicle.

They will be administered either orally, in the form of tablets, pills or capsules, at a posology up to 500 mg/day of active ingredient, or parenterally, in the form of an aqueous injectable solution at a posology up to 50 mg/day of active ingredient.

We claim:
1. A compound corresponding to the formula:

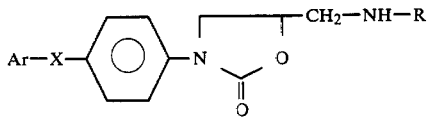

wherein R represents:
a hydrogen atom, in which case Ar—X represents an element selected from the group consisting of:

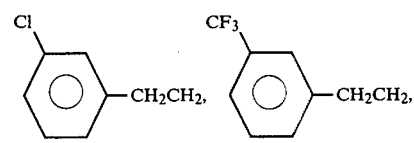

-continued

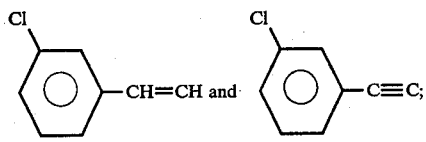

an alkyl group having 1 to 4 carbon atoms, in which case Ar—X represents either

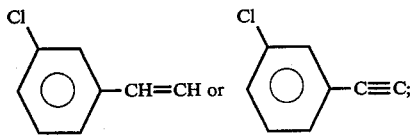

a propargyl group, in which case Ar—X the group

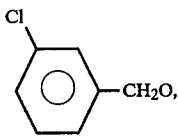

and the acid addition salts thereof.

2. A compound according to claim 1 wherein R is methyl.

3. A compound according to claim 1 wherein said acid addition salt is a salt formed from hydrochloric acid.

4. A pharmaceutical composition for treating troubles of the central nervous system and senescence, comprising an effective amount of a compound according to claim 1 in combination with a pharmaceutically acceptable carrier, diluent or vehicle.

5. A method for treating a subject suffering from troubles of the central nervous system or senescence, comprising administering to said subject a therapeutically effective amount of the composition of claim 4.

* * * * *